(12) United States Patent
Schulz et al.

(10) Patent No.: US 8,609,799 B2
(45) Date of Patent: Dec. 17, 2013

(54) METHOD OF FORMING FUNCTIONALIZED SILANES

(75) Inventors: Douglas L. Schulz, Moorhead, MN (US); Xuliang Dai, Fargo, ND (US); Kendric J. Nelson, La Crosse, WI (US); Philip Boudjouk, Fargo, ND (US)

(73) Assignee: NDSU Research Foundation, Fargo, ND (US)

( * ) Notice: Subject to any disclaimer, the term of this patent is extended or adjusted under 35 U.S.C. 154(b) by 518 days.

(21) Appl. No.: 12/993,239

(22) PCT Filed: May 26, 2009

(86) PCT No.: PCT/US2009/045132
§ 371 (c)(1),
(2), (4) Date: Jan. 5, 2011

(87) PCT Pub. No.: WO2009/148878
PCT Pub. Date: Dec. 10, 2009

(65) Prior Publication Data
US 2011/0108777 A1    May 12, 2011

Related U.S. Application Data

(60) Provisional application No. 61/130,271, filed on May 29, 2008.

(51) Int. Cl.
*C08G 77/30* (2006.01)
(52) U.S. Cl.
USPC ............... 528/23; 423/341; 423/342; 528/10; 528/33; 528/37
(58) Field of Classification Search
USPC .................... 423/341, 342; 528/10, 23, 33, 37
See application file for complete search history.

(56) References Cited

U.S. PATENT DOCUMENTS

| | | | |
|---|---|---|---|
| 4,447,633 A | 5/1984 | Boudjouk | |
| 4,657,777 A | 4/1987 | Hirooka et al. | |
| 4,683,147 A | 7/1987 | Eguchi et al. | |
| 4,695,331 A | 9/1987 | Ramaprasad | |
| 4,827,009 A | 5/1989 | Boudjouk | |
| 4,841,083 A | 6/1989 | Nagai et al. | |
| 4,910,153 A | 3/1990 | Dickson | |
| 5,942,637 A | 8/1999 | Boudjouk et al. | |
| 6,503,570 B2 | 1/2003 | Matsuki et al. | |
| 6,518,087 B1 | 2/2003 | Furusawa et al. | |
| 6,527,847 B1 | 3/2003 | Matsuki | |
| 6,541,354 B1 | 4/2003 | Shimoda et al. | |
| 6,743,738 B2 | 6/2004 | Todd | |
| 6,767,775 B1 | 7/2004 | Yudasaka et al. | |
| 6,846,513 B2 | 1/2005 | Furusawa et al. | |
| 7,052,980 B2 | 5/2006 | Aoki | |
| 7,067,069 B2 | 6/2006 | Shiho et al. | |
| 7,173,180 B2 | 2/2007 | Shiho et al. | |
| 7,223,802 B2 | 5/2007 | Aoki et al. | |
| 7,314,513 B1 | 1/2008 | Zürcher et al. | |
| 7,422,708 B2 | 9/2008 | Kunze et al. | |
| 7,485,691 B1 | 2/2009 | Guo et al. | |
| 7,491,782 B1 | 2/2009 | Guo et al. | |
| 7,498,015 B1 | 3/2009 | Kunze et al. | |
| 7,531,588 B2 | 5/2009 | Weller et al. | |
| 7,553,545 B2 | 6/2009 | Kunze et al. | |
| 7,674,926 B1 | 3/2010 | Guo et al. | |
| 7,723,457 B1 | 5/2010 | Guo et al. | |
| 7,767,261 B2 | 8/2010 | Kunze et al. | |
| 7,799,302 B1 | 9/2010 | Kunze et al. | |
| 7,879,696 B2 | 2/2011 | Kunze et al. | |
| 7,943,721 B2 | 5/2011 | Dioumaev | |
| 7,951,892 B1 | 5/2011 | Guo et al. | |
| 2001/0021760 A1 | 9/2001 | Matsuki et al. | |
| 2003/0229190 A1 | 12/2003 | Aoki et al. | |
| 2005/0145163 A1 | 7/2005 | Matsuki et al. | |
| 2006/0185712 A1 | 8/2006 | Shiho et al. | |
| 2006/0281841 A1 | 12/2006 | Weller et al. | |

FOREIGN PATENT DOCUMENTS

WO    WO 00/59014    10/2000

OTHER PUBLICATIONS

International Search Report and Written Opinion for PCT/US2009/045132, mail date Feb. 24, 2010, 7 pages.
Amberger et al., "The Preparation of Trisilylphosphine," Angew. Chem. Int. Ed. Engl., vol. 1, 1962, No. 1, p. 52.
Anderson, "n-Butylhalosilanes. Determination of Silane Hydrogen in Liquids," Contribution from the Chemistry Department, Drexel Institute of Technology, Mar. 20, 1960, pp. 1323-1325.
Choi et al., "Amine-Promoted Disproportionation and Redistribution of Trichlorosilane: Formation of Tetradecachlorocyclohexasilane Dianion," Journal of American Chemical Society, vol. 123, pp. 8117-8118 (2001).
Fritz et al., "Silylphosphanes: Developments in Phosphorus Chemistry," Chem. Rev. 2000, vol. 100, pp. 3341-3401.
Gaines et al., "Synthesis of Bis(pentaboranyl)-Group IV Compounds," Inorganic Chemistry, vol. 13, No. 12, 1974, pp. 2792-2796.
Gokhale et al.,"Disilanylphosphine and Dsilylphosphine," Inorganic Chemistry, 1964, vol. 3 (8), pp. 1141-1143.
Gollner et al., "Linear and Cyclic Polysilanes Containing the Bis(trimethylsilyl)amino Group: Synthesis, Reactions and Spectroscopic Characterization," Inorganic Chemistry, vol. 42, No. 15, 2003, pp. 4579-4584.
Han et al., "Printed Silicon As Diode and FET Materials—Preliminary Results," Journal of Non-Crystalline Solids, vol. 354, 2008, pp. 2623-2626.
Han et al., "Doped and Undoped Si Films Made from Cyclohexasilane," Spring 2008 Materials Research Society Meeting, San Francisco, CA, Mar. 25, 2008, 1 page.
Hengge et al., "Preparation of Cyclohexasilane, $Si_6H_{12}$," Angew. Chem. Int. Ed. Engl., vol. 16, 1977, No. 6, p. 403.

(Continued)

*Primary Examiner* — Mark Kopec
*Assistant Examiner* — Haidung Nguyen
(74) *Attorney, Agent, or Firm* — Foley & Lardner LLP

(57) ABSTRACT

Heteroatom doped silane compounds, e.g., phosphorus-containing silane compounds, are provided. The application also provides methods of producing the heteroatom doped silane compounds from halogen substituted silanes via reaction with a heteroatom-containing nucleophile.

23 Claims, 3 Drawing Sheets

(56) References Cited

OTHER PUBLICATIONS

Herzog et al., "Preparation of Oligosilanes Containing Perhalogenated Silyl Groups and their Hydrogenation by Stannanes," Journal of Organometallic Chemistry 544, 1997, pp. 217-223.

Holbling et al., "The Cyclohexasilanes $Si_6H_{11}X$ and $Si_6Me_{11}X$ with X=F, Ci, Br and I: A Quantum Chemical and Raman Spectroscopic Investigation of a Multiple Conformer Problem," Chem. Phys. Chem. 2007, vol. 8, pp. 735-744.

Kaczmarczyk et al., "A New Synthesis for Hexasilicon Tetradecachloride,[1] $Si_6Cl_{14}$," Journal of American Chemical Society, vol. 82, 1960, pp. 751-752.

Kaczmarczyk et al., "A New Pentasilicon Dodecachlorida, $Si_5Cl_{12}$," Journal of Inorganic Nuclear Chemistry, 1961, vol. 17, pp. 186-188.

Norman et al., "The Lithium Tetraphosphinnoaluminate Phosphination of Halosilanes and Germanes," Inorganic Chemistry, 1970, vol. 9 (1), pp. 98-103.

Poschl et al., "Synthesis and Spectroscopy of Halogenated Cyclopentasilanes," Organometallics 1996, vol. 15, No. 14, pp. 3238-3240.

Sevast'Yanov et al., "Perchlorosilanes and Perchlorocarbosilanes as Precursors for SiC Synthesis," Inorganic Materials, vol. 43, No. 4, Pleiades Publishing, Inc. (2007), pp. 369-372.

Shono et al., "Electroreductive Synthesis of Polygermane and Germane-Silane Copolymer," J. Chem Soc., Chem Commun. 1992, pp. 896-897.

Tanaka et al., "Spin-on n-Type Silicon Films Using Phosphorous-doped Polysilanes," Japanese Journal of Applied Physics, vol. 46, No. 36, 2007, pp. L886-L888.

Vanderwielen et al., "An Examination of the Chlorination of Silanes by Silver Chloride," Inorganic Chemistry, vol. 11, No. 2, 1972, pp. 246-250.

Wiberg et al., "Cleavage Reactions with the Chlorosilanes $Si_2Cl_6$, $Si_3Cl_8$, and $Si_5Cl_{12}$,," Angew, Chem. Internation, Edit. vol. 1, 1962, No. 9, p. 517.

Wingeleth et al., "Redistribution of Primary Silyl—and Germyphosphines :Synthesis of Trisilyl—and Trigermylphosphines," Phosphorous and Sulfur and Related Elements, 1988, vol. 39 (1-2), pp. 123-129.

METHOD OF FORMING FUNCTIONALIZED SILANES

CROSS-REFERENCE TO RELATED PATENT APPLICATIONS

This patent application is a U.S. national stage of International Application No. PCT/US2009/045132, filed on May 26, 2009, entitled "METHOD OF FORMING FUNCTIONALIZED SILANES," which claims the benefit of U.S. Provisional Application No. 61/130,271, filed on May 29, 2008, entitled "METHOD OF FORMING FUNCTIONALIZED SILANES."

GOVERNMENT RIGHTS STATEMENT

This invention was made with government support under Grant No. DMEA H94003-08-2-0801 awarded by the Defense Microelectronics Activity and under Grant No. EPS-0447679 awarded by the National Science Foundation. The U.S. Government has certain rights in the invention.

BACKGROUND

While polymers have been a focus of evaluation as flexible layers in electronic materials, more recently there has been an interest in developing printed routes to inorganic semiconductors as a means of achieving higher mobilities. To utilize cost-effective polymeric substrates in a roll-to-roll manufacturing environment, low-temperature atmospheric pressure deposition routes to semi-conductors with desirable electrical properties are required. Cyclic silanes, such as cyclohexasilane, have been shown to be useful in liquid silane precursors to a-Si:H rectifying diodes and field effect transistors. The liquid cyclic silanes reportedly can be transformed into amorphous silicon and subsequently to crystalline Si under appropriate conditions. The initial studies reported potential non-uniform dopant distribution, when simple inorganic boron or phosphorus compounds, which may tend to congregate at the film surface, when employed as dopants. Such non-uniform doping may lead to suboptimal electrical properties in the resulting semi-conductor film. The availability of liquid silanes which contain one or more heteroatom dopants covalently bound to a silane backbone offer the potential to provide good miscibility with other silanes and permit atomic level mixing and uniform dopant distributions.

SUMMARY

The present application is directed to heteroatom doped silane compounds and methods of producing such compounds. The methods commonly includes reacting a halogen substituted silane with a nucleophilic reagent to form a doped silane with a Si-E bond, where "E" may be selected from Group 13, Group 14, Group 15 and/or Group 16 elements. The doped silane is desirably a liquid under ambient temperature and pressure conditions (e.g., under 1 atmosphere pressure at 298° C.).

The halogen substituted silane may be formed by reacting a cyclic or acyclic silane with a halogenating reagent. In other embodiments, the halogen substituted silane may be formed by reacting an aryl substituted (e.g., phenyl substituted) cyclic or acyclic silane with a hydrogen halide in the presence of a Lewis acid catalyst, such as AlCl$_3$. In certain embodiments, it may be advantageous to control the starting materials, reaction conditions and/or stoichiometry, such that the reaction product is predominantly a monohalogen substituted and/or dihalogen substituted silane. Monohalogen substituted cyclic silanes, such as monochlorocyclopentasilane, monochlorocyclohexasilane, monobromocyclopentasilane and monobromocyclohexasilane, may be particularly desirable as intermediates for use in producing the present doped silane compounds.

The present heteroatom doped silane compounds may have the formula:

$$Si_nH_{m-y}(EH_z)_y$$

wherein n is an integer greater than 2; m is an integer from 2n−2 to 2n+2; y is an integer from 1 to n; z is 2 or 3; and E is selected from Group 13, Group 14, Group 15 and/or Group 16 elements.

Examples of the present heteroatom doped silane compounds include cyclic silane compounds having the formula:

$$Si_nH_{m-y}(PH_2)_y$$

wherein n is an integer greater than 2 (commonly 3 to 10); m is 2n−2 or 2n; and y is an integer from 1 to n.

Other examples of the present heteroatom doped silane compounds include acyclic silane compounds (e.g., branched and/or linear silanes), which are desirably a liquid under ambient temperature and pressure, having the formula:

$$Si_nH_{m-y}(PH_2)_y$$

wherein n is an integer greater than 2; m is 2n+2; and y is an integer from 1 to n.

In certain embodiments, it may be advantageous to produce doped silane compounds which only have one or two heteroatoms per molecule. Suitable synthetic intermediates which may be used to produce such heteroatom doped silane compounds include halogen substituted cyclic silane compounds having the formula:

$$Si_nH_{m-y}X_y$$

wherein n is an integer greater than 2 (commonly about 3 to 10); m is an integer from 2n−2 to 2n; y is 1 or 2; and each X independently represents a halogen atom. Suitable examples include mono- or dihalogenated derivatives of cyclotrisilane, cyclopentasilane, cyclohexasilane, silylcyclopentasilane, silylcyclohexasilane and spiro[4.4]nonasilane.

In certain embodiments, the present heteroatom doped silane compounds may be prepared by reacting a mixture comprising:

$$Si_nH_{m-y}X_y$$

with a nucleophile of the formula:

$$M(EH_z)_a$$

to provide a doped silane compound of the formula:

$$Si_nH_{m-y}(EH_z)_y$$

In the above formulas, n is an integer greater than 2; m is an integer from 2n−2 to 2n+2; y is an integer from 1 to n. E is a heteroatom chosen from Group 13, Group 14, Group 15 and/or Group 16 elements; z is 2 or 3; a is an integer from 1 to 4; and M is a metal atom containing moiety. The reaction is typically carried out in the presence of a solvent, e.g., an ether solvent such as glyme, diglyme or the like. For example, the halogenated silane may be reacted with a nucleophile of the formula:

$$M(PH_2)_a.$$

Suitable examples of such nucleophiles include NaPH$_2$, LiPH$_2$, NaAl(PH$_2$)$_4$ and LiAl(PH$_2$)$_4$.

In certain embodiments, the present application provides a method of producing a halogenated cyclic silane of the formula:

$$Si_nH_{m-y}X_y$$

wherein n is an integer greater than 2 (commonly about 3 to 10); m is 2n−2 or 2n; y is 1 or 2; and each X independently represents a halogen atom. The method includes reacting a cyclic silane (e.g., either a monocyclic or bicyclic) with a halogenating agent to provide a halo-silane having a formula:

$$Si_nH_{m-y}X_y$$

wherein n is an integer greater than 2 (commonly about 3 to 10; m is an integer from 2n−2 to 2n; y is 1 or 2; and each X independently represents a halogen atom. Examples of suitable halogenating agents include AgCl, HgCl$_2$, HgBr$_2$, N-chlorosuccinimide ("NCS"), N-bromosuccinimide ("NBS"), SnCl$_4$ and iodine (I$_2$).

In other embodiments, heteroatom doped silane compounds may be prepared by reacting a mixture comprising:

$$Si_nH_{m-y}X_y$$

with other phosphorus-containing nucleophiles. For example, halogenated silanes may be reacted with phosphorus-containing nucleophiles of the formula:

$$M^*PHSiH_3$$

where M* is an alkali metal (e.g., Li) to provide a heteroatom doped silane having a formula:

$$Si_nH_{m-y}(PHSiH_3)_y$$

wherein n is an integer greater than 2; m is an integer from 2n−2 to 2n+2; and y is an integer from 1 to n (and often desirably 1 or 2).

In certain other embodiments, heteroatom doped silane compounds may be prepared by reacting a mixture comprising:

$$Si_nH_{m-y}X_y$$

with phosphorus-containing nucleophiles of the formula:

$$M^*P(SiH_3)_2$$

where M* is an alkali metal (e.g., Li) to provide a heteroatom doped silane having a formula:

$$Si_nH_{m-y}(P(SiH_3)_2)_y$$

wherein n is an integer greater than 2; m is an integer from 2n−2 to 2n+2; and y is an integer from 1 to n (and often desirably 1 or 2).

DETAILED DESCRIPTION

Figure 1:
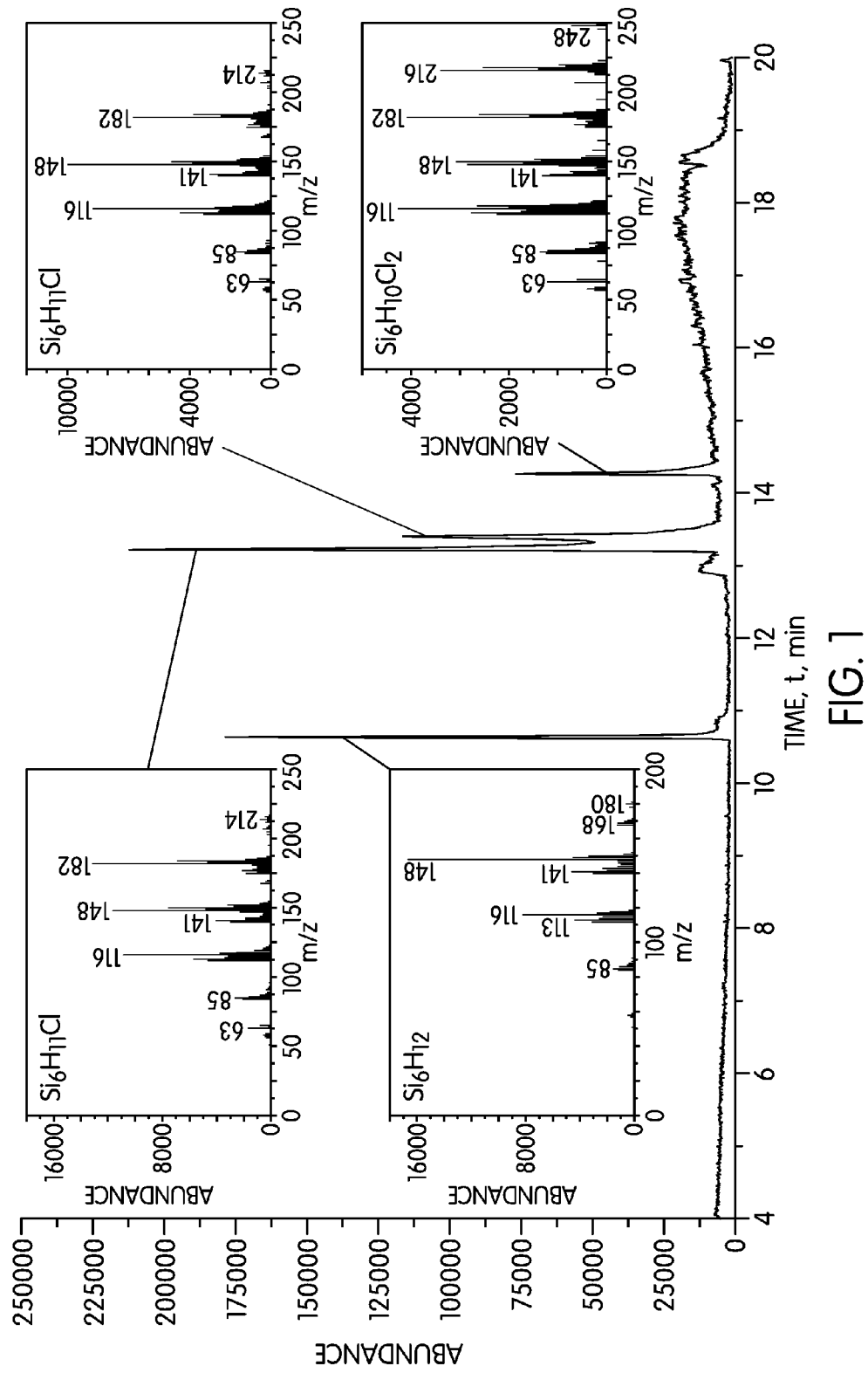
FIG. 1 depicts a GC-MS of the product solution produced according to the procedure described in Example 1.

The present heteroatom doped silane compounds may be produced by reacting a halogen substituted silane with a nucleophilic reagent to form the doped silane. For example, a halogenated silane may be reacted with a phosphorus-containing nucleophile to form a compound which includes a Si—P bond. The resulting product, a phosphorus doped silane, is desirably a liquid under ambient temperature and pressure (e.g., under 1 atmosphere pressure at 298° C.).

The halogen substituted silane may be formed by reacting a cyclic or acyclic silane with a halogenating reagent. In some embodiments, the starting materials, reaction conditions and/or stoichiometry may be controlled such that the reaction product is predominantly a silane substituted with only one or two halogen atoms. The halogenation reaction is typically carried out in the presence of a solvent, e.g., a chlorinated hydrocarbon solvent such as methylene chloride, chloroform, carbon tetrachloride and/or dichloroethane.

In some embodiments, the halogen substituted silane may be formed by dissolving a silane compound, e.g., a cyclic silane such as cyclotrisilane, cyclopentasilane or cyclohexasilane, in a chlorinated solvent (e.g., methylene chloride) and stirring the solution of silane with an inorganic halogenating reagent, such as AgCl, HgCl$_2$, HgBr$_2$, BCl$_3$, or SnCl$_4$. In such cases, an excess of the halogenating reagent may be used. After stirring the reaction mixture for a period of several hours, a mixture containing mono- and dihalogenated silane is typically obtained.

In other embodiments, a silane compound, e.g., a cyclic silane such as cyclotrisilane, cyclopentasilane or cyclohexasilane, may be dissolved in a chlorinated solvent (e.g., methylene chloride or carbon tetrachloride) and a stoichiometric amount of N-chlorosuccinimide ("NCS") or N-bromosuccinimide ("NBS") added to the solution. By stoichiometric amount is meant that one equivalent of the halogenating reagent is added for each halogen desired to be added to the silane. For example, if monohalogenated silanes are the desired products, one mole of NBS or NCS is added to the solution for each mole of silane. If dihalogenated silanes are the desired products, two moles of NBS or NCS are added to the solution for each mole of silane.

Examples of suitable halogenated silane intermediates include:
  cyclotrisilane having 1 or 2 halogen atoms attached thereto;
  cyclopentasilane having 1 or 2 halogen atoms attached thereto;
  cyclohexasilane having 1 or 2 halogen atoms attached thereto;
  silylcyclopentasilane having 1 or 2 halogen atoms attached thereto;
  silylcyclohexasilane having 1 or 2 halogen atoms attached thereto; and
  spiro[4.4]nonasilane having 1 or 2 halogen atoms attached thereto.

Halogenated silane compounds, which may be used to produce the present heteroatom doped silane compounds may be produced by reacting a halogenating reagent with a corresponding silane precursor. Examples of suitable halogenating reagents include:
  AgCl, HgCl$_2$, HgBr$_2$, SnCl$_4$, I$_2$, N-chlorosuccinimide ("NCS"), and
  N-bromosuccinimide ("NBS").

Examples of suitable phosphorus-containing nucleophiles which may be used to produce the present heteroatom doped silane compounds include:
  LiPH$_2$, NaPH$_2$, KPH$_2$, LiAl(PH$_2$)$_4$, NaAl(PH$_2$)$_4$, LiHPSiH$_3$, LiP(SiH$_3$)$_2$ and LiAl(PHSiH$_3$)$_4$.

EXAMPLES

Reference is made in the following to a number of illustrative examples of methods of producing the present compositions. The following embodiments should be considered as only an illustration of such methods and compositions and should not be considered to be limiting in any way.

Example 1

AgCl Route Towards $Si_6H_{12-n}Cl_n$ (Where n=1, 2)

The desired chlorosilane product, $Si_6H_{12-n}Cl_n$ (where n=1, 2) was prepared by dissolving 185.5 mg (1.03 mmol, 1.00 eq) of cyclohexasilane, $Si_6H_{12}$, in 2 mL of methylene chloride ($CH_2Cl_2$) to which an excess amount (515.4 mg, 3.60 mmol, 3.50 eq) of silver chloride, AgCl, was added as a solid with vigorous stirring. The reaction mixture was allowed to stir in the dark as a consequence of the light sensitivity of silver compounds. After stirring for 3.5 h at room temperature (25° C.) the reaction mixture was a dark grey color which was indicative of silver metal, $Ag^0$, forming. This mixture was filtered to remove the grey colored precipitate (ppt) yielding a clear colorless solution. This product solution was analyzed by GC-MS (see FIG. 1) which established that 69.1% of the $Si_6H_{12}$ was converted to the mono-chlorocyclohexasilane, $Si_6H_{11}Cl$, and 11.8% was converted to the dichlorocyclohexasilane, $Si_6H_{10}Cl_2$. Therefore, 19.1% of the $Si_6H_{12}$ starting material remained unreacted.

Example 2

$HgCl_2$ Route Towards $Si_6H_{12-n}Cl_n$ (Where n=1, 2)

Figure 2:
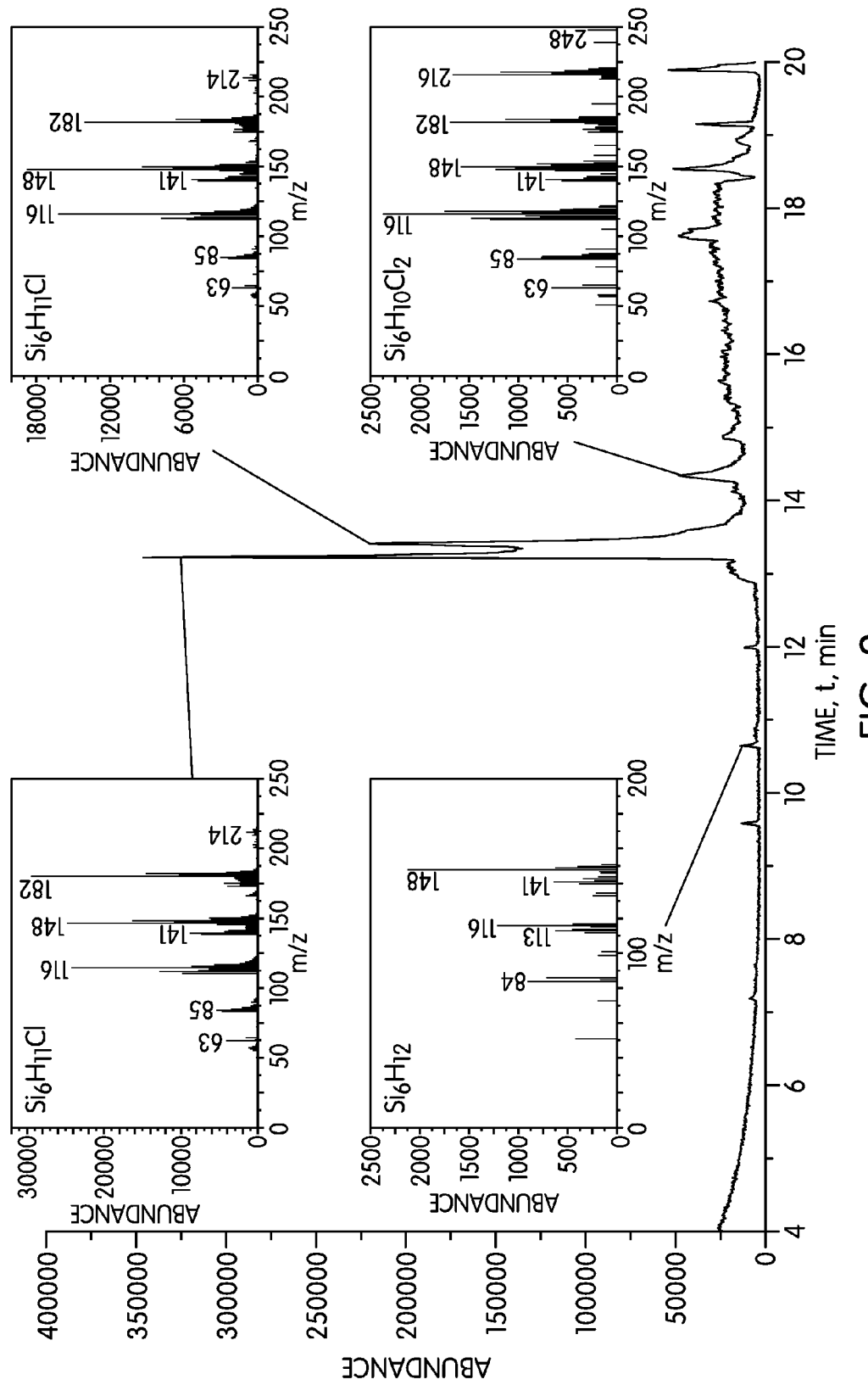
FIG. 2 depicts GC-MS of the product solution produced according to the procedure described in Example 2.

The desired chlorosilane product, $Si_6H_{12-n}Cl_n$ (where n=1, 2) was prepared by dissolving 217.5 mg (1.20 mmol, 1.00 eq) of $Si_6H_{12}$ in 5 mL of $CH_2Cl_2$ to which an excess amount (1.31 g, 4.81 mmol, 4.00 eq) of mercury(II) chloride, $HgCl_2$, was slowly added as a solid with vigorous stirring. Initially there appeared to be no observable reaction, therefore, the reaction mixture was allowed to stir. Overnight liquid mercury had formed suggesting the desired reaction had taken place. The solution mixture was filtered to remove unreacted $HgCl_2$. This was done by careful decantation of the solution mixture from the liquid mercury byproduct that formed. Once filtered the filtrate was a clear colorless solution. The product solution was analyzed by GC-MS (FIG. 2) concluding that 91.5% of the $Si_6H_{12}$ was converted into $Si_6H_{11}Cl$ and 7.6% converted to $Si_6H_{10}Cl_2$. Therefore, 0.9% of unreacted $Si_6H_{12}$ was remaining

Example 3

$SnCl_4$ Route Towards $Si_6H_{12-n}Cl_n$ (Where n=1, 2)

The desired chlorosilane product, $Si_6H_{12-n}Cl_n$ (where n=1, 2) was prepared by first dissolving 2.40 g (13.33 mmol) of $Si_6H_{12}$ in 30 mL of $CH_2Cl_2$ in a 100 mL flask. This solution was then cooled to −10° C. at which point an excess of $SnCl_4$ (5.20 g, 20 mmol) was added into the mixture. The reaction was stirred vigorously for two minutes and then stored in freezer (−10° C.) for two days. White precipitate formed was removed by filtration and the filtrate was distilled under vacuum to give 1.8 g colorless liquid. The product liquid was analyzed by GC-MS concluding that 65% of the $Si_6H_{12}$ was converted into $Si_6H_{11}Cl$ and 5% converted to $Si_6H_{10}Cl_2$. Therefore, 30% of unrected $Si_6H_{12}$ was remaining.

Example 4

Figure 3:
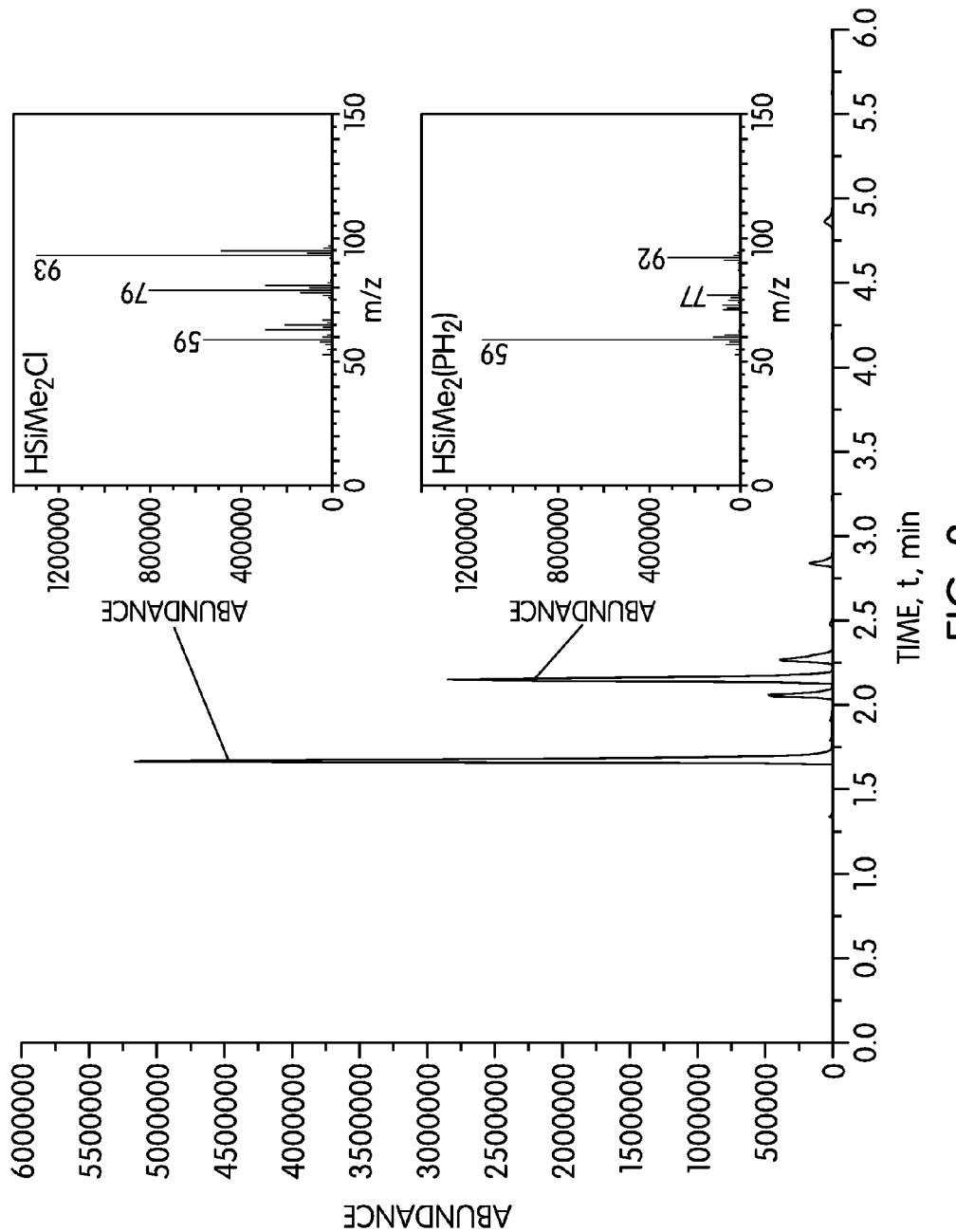
FIG. 3 depicts GC-MS of the product solution produced according to the procedure described in Example 2 displaying Si—P bond formation.

Formation of $H_2PHSiMe_2$ via $NaAl(PH_2)_4$ $NaAl(PH_2)_4$ was synthesized by reacting 50.4 mg of $NaPH_2$ (0.90 mmol, 1.00 eq) suspended in 2 mL of diethylene glycol dimethyl ether (diglyme) with 30.8 mg of $AlCl_3$ (0.231 mmol, 3.90 eq) dissolved in 1 mL which resulted in the formation of a cloudy white slurry. This white precipitate is consistent with the formation of sodium chloride, NaCl. The $AlCl_3$ was quantitatively transferred by washing the vial with 3×1 mL of diglyme resulting in a 6 mL mixture that was allowed to stir overnight. After stirring overnight the reaction mixture was filtered yielding a faint yellow clear filtrate and a white solid. The solids were washed with 3×1 mL diglyme to quantitatively transfer the desired product in solution. To this stirring solution of $NaAl(PH_2)_4$, 103 μL of chlorodimethylsilane (0.852 g/mL, 0.93 mmol, 4.01 eq), $HSiMe_2Cl$, was added via micro-syringe addition resulting in the formation of a cloudy solution. The cloudiness is due to the formation of the NaCl byproduct. The mixture was allowed to stir for 10 min after which was filtered yielding a faint yellow product solution. This product filtrate was analyzed by GC-MS (FIG. 3) and showed the formation of the desired Si—P containing product of $H_2PHSiMe_2$.

Illustrative Embodiments

Reference is made in the following to a number of illustrative embodiments of the subject matter described herein. The following embodiments describe illustrative embodiments that may include various features, characteristics, and advantages of the subject matter as presently described. Accordingly, the following embodiments should not be considered as being comprehensive of all of the possible embodiments or otherwise limit the scope of the methods materials and coatings described herein.

One embodiment provides a method of preparing a doped silane which includes reacting a mixture comprising:

$Si_nH_{m-y}X_y$ and $MPH_2$ to provide a heteroatom doped silane having a formula:

$Si_nH_{m-y}(PH_2)_y$.

wherein n is an integer greater than 2; m is an integer from 2n−2 to 2n+2; y is an integer from 1 to n; each X is independently a halogen atom; and M is a metal atom containing moiety. Suitable examples of $MPH_2$ include:

$LiPH_2$, $NaPH_2$, $KPH_2$, $LiAl(PH_2)_4$ and $NaAl(PH_2)_4$.

In this embodiment, the method may include reacting $Si_nH_{2n-y}X_y$ with $NaPH_2$
or reacting $Si_nH_{2n-y}X_y$ with $NaAl(PH_2)_4$; e.g., reacting $Si_6H_{11}Cl$ with $NaAl(PH_2)_4$;

$Si_5H_9Cl$ with $NaAl(PH_2)_4$;

$Si_3H_5Cl$ with $NaAl(PH_2)_4$; or $Si_7H_{13}Cl$ with $NaAl(PH_2)_4$.

In another embodiment, a heteroatom doped silane compound may be formed by reacting a mixture, which includes:

$Si_nH_{m-y}X_y$ and $LiP(SiH_3)_2$ to provide a heteroatom doped silane having a formula:

$Si_nH_{m-y}(P(SiH_3)_2)_y$.

wherein n is an integer greater than 2; m is an integer from 2n−2 to 2n+2; and y is an integer from 1 to n.

In another embodiment, a heteroatom doped silane compound may be formed by reacting a mixture, which includes:

$Si_nH_{m-y}X_y$ and $LiPHSiH_3$ to provide a heteroatom doped silane having a formula:

$$Si_nH_{m-y}(PHSiH_3)_y$$

wherein n is an integer greater than 2; m is an integer from 2n−2 to 2n+2; and y is an integer from 1 to n.

Suitable examples of the present heteroatom doped silane compounds include doped silanes having a formula:

$$Si_nH_{m-y}(PH_2)_y$$

wherein n is an integer greater than 2; m is an integer from 2n−2 to 2n+2; and y is an integer from 1 to n, often y is 1 or 2. The present heteroatom doped silane compounds may desirably include compounds having one or more of the following formulas:

$$Si_6H_{11}(PH_2);$$

$$Si_6H_{10}(PH_2)_2;$$

$$Si_5H_9(PH_2); \text{ and}$$

$$Si_5H_8(PH_2)_2.$$

Other examples of the present heteroatom doped silane compounds include doped cyclic silanes having a formula:

$$Si_nH_{m-y}(PH_2)_y$$

wherein n is an integer from 3 to 10; m is 2n−2 or 2n; and y is an integer from 1 to n.

Other examples of the present heteroatom doped silane compounds include doped silanes having a formula:

$$Si_nH_{m-y}(P(SiH_3)_2)_y$$

wherein n is an integer greater than 2 (typically 3 to 10); m is an integer from 2n−2 to 2n+2; and y is an integer from 1 to n (and often desirably 1 or 2).

Other examples of the present heteroatom doped silane compounds include doped silanes having a formula:

$$Si_nH_{m-y}(PHSiH_3)_y$$

wherein n is an integer greater than 2 (typically 3 to 10); m is an integer from 2n−2 to 2n+2; and y is an integer from 1 to n (and often desirably 1 or 2).

Certain embodiments provide halogen substituted cyclic silanes having the formula:

$$Si_nH_{m-y}X_y$$

wherein n is an integer greater than 2 (commonly 3 to 10); m is 2n or 2n−2; y is 1 or 2; and each X independently represents a halogen atom. Suitable examples include:
- such halogen substituted cyclic silanes wherein n is 3; m is 6; y is 1; and X is a chlorine atom;
- such halogen substituted cyclic silanes wherein n is 5; m is 10; y is 1; and X is a chlorine atom;
- such halogen substituted cyclic silanes wherein n is 6; m is 12; y is 1; and X is a chlorine atom; or
- such halogen substituted cyclic silanes wherein n is 7; m is 14; y is 1; and X is a chlorine atom.

Additional suitable examples of halogen substituted cyclic silanes include:
- such halogen substituted cyclic silanes wherein n is 3; m is 6; y is 1; and X is a bromine atom;
- such halogen substituted cyclic silanes wherein n is 5; m is 10; y is 1; and X is a bromine atom;
- such halogen substituted cyclic silanes wherein n is 6; m is 12; y is 1; and X is a bromine atom; or
- such halogen substituted cyclic silanes wherein n is 7; m is 14; y is 1; and X is a bromine atom.

Other examples of suitable halogen substituted cyclic silanes include:
- chlorocyclopentasilane and/or dichlorocyclopentasilane;
- chlorocyclohexasilane and/or dichlorocyclohexasilane;
- monochloro- and/or dichloro-derivatives of silylcyclohexasilane;
- monochloro- and/or dichloro-derivatives of silylcyclopentasilane;
- monochloro- and/or dichloro-derivative of spiro[4.4]nonasilane;
- silylcyclopentasilane having 1 and/or 2 chlorine substituents;
- spiro[4.4]nonasilane having 1 and/or 2 chlorine substituents;
- silylcyclohexasilane having 1 and/or 2 chlorine substituents;
- cyclohexasilane having 1 and/or 2 chlorine substituents;
- cyclopentasilane having 1 and/or 2 chlorine substituents; and
- cyclotrisilane having 1 and/or 2 chlorine substituents.

Other examples of suitable halogen substituted cyclic silanes include:
- bromocyclopentasilane and/or dibromocyclopentasilane;
- bromocyclohexasilane and/or dibromocyclohexasilane;
- monobromo- and/or dibromo-derivatives of silylcyclohexasilane;
- monobromo- and/or dibromo-derivatives of silylcyclopentasilane;
- monobromo- and/or dibromo-derivative of spiro[4.4]nonasilane;
- silylcyclopentasilane having 1 and/or 2 bromine substituents;
- spiro[4.4]nonasilane having 1 and/or 2 bromine substituents;
- silylcyclohexasilane having 1 and/or 2 bromine substituents;
- cyclohexasilane having 1 and/or 2 bromine substituents;
- cyclopentasilane having 1 and/or 2 bromine substituents; and
- cyclotrisilane having 1 and/or 2 bromine substituents.

It will be readily apparent to one skilled in the art that varying substitutions and modifications may be made to the methods and compositions disclosed herein without departing from the scope and spirit of the invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

What is claimed is:

1. A doped silane having a formula:

$$Si_nH_{m-y}(PR'R)_y$$

wherein n is an integer greater than 2; m is 2n or 2n−2; R and R' are independently H or SiH$_3$; and y is an integer from 1 to n.

2. The doped silane of claim 1 wherein said silane is a cyclic compound having the formula:

$$Si_nH_{m-y}(PH_2)_y$$

wherein n is an integer from 3 to 10; m is 2n−2 or 2n; and y is an integer from 1 to n.

3. The doped silane of claim 1 wherein n is an integer from 3 to 10.

4. The doped silane of claim 1 wherein said silane is cyclopentasilane having 1 or 2 —PH$_2$ moieties attached thereto.

5. The doped silane of claim 1 wherein said silane is cyclohexasilane having 1 or 2 —PH$_2$ moieties attached thereto.

6. The doped silane of claim 1 wherein said silane is silylcyclopentasilane having 1 or 2 —PH$_2$ moieties attached thereto.

7. The doped silane of claim 1 wherein said silane is spiro[4.4]nonasilane having 1 or 2 —PH$_2$ moieties attached thereto.

8. The doped silane of claim 1 wherein m is 2n.

9. The doped silane of claim 1 wherein m is 2n−2.

10. The doped silane of claim 1 having the formula:

$$Si_6H_{11}(PH_2)$$

11. The doped silane of claim 1 having the formula:

$$Si_6H_{10}(PH_2)_2$$

12. The doped silane of claim 1 having the formula:

$$Si_5H_9(PH_2)$$

13. The doped silane of claim 1 having the formula:

$$Si_5H_8(PH_2)_2$$

14. The doped silane of claim 1, wherein said doped silane has a formula:

$$Si_nH_{m-y}(P(SiH_3)R)_y$$

wherein n is an integer from 3 to 10; m is 2n−2 or 2n; R is H or SiH$_3$ j and y is 1 or 2.

15. The doped silane of claim 1, wherein said doped silane has a formula:

$$Si_nH_{2n-y}(P(SiH_3)_2)_y$$

wherein n is an integer from 3 to 7; and y is 1 or 2.

16. A method of preparing a doped silane comprising reacting a mixture comprising:

$$Si_nH_{m-y}X_y \text{ and } M(PR'R)_z$$

to provide a heteroatom doped silane having a formula:

$$Si_nH_{m-y}(PR'R)_y$$

wherein n is an integer from 3 to 10; m is 2n or 2n−2 to 2n+2; y is 1 or 2; Z is an integer from 1 to 4; each X is independently a halogen atom; R and R' are independently H or SiH$_3$; and M is a metal atom containing moiety.

17. The method of claim 16, wherein preparing the doped silane comprises reacting a mixture comprising:

$$\text{the } Si_nH_{m-y}X_y \text{ and } M*PRSiH_3$$

to provide a heteroatom doped silane having a formula:

$$Si_nH_{m-y}(PRSiH_4)_y$$

wherein M* is an alkali metal; R is H or SiH$_3$ and each X independently represents a chlorine or bromine atom.

18. The method of claim 17 wherein M*PRSiH$_3$ is: LiPHSiH$_3$ and/or LiP(SiH$_3$)$_2$.

19. The method of claim 16 wherein the halogen atom is a bromine and/or chlorine atom.

20. The method of claim 16, wherein preparing the doped silane comprises reacting a mixture comprising:

$$M(PH_2)_z \text{ and the } Si_nH_{m-y}X_y$$

to provide a doped silane having a formula:

$$Si_nH_{m-y}(PH_2)_y$$

wherein Z is an integer from 1 to 4; and M is a metal atom containing moiety.

21. The method of claim 20 wherein M(PH$_2$)$_z$ is: LiPH$_2$, NaPH$_2$, KPH$_2$, LiAl(PH$_2$)$_4$, or NaAl(PH$_2$)$_4$.

22. The method of claim 16, wherein n is 5 or 6; m is 2n; and X is a chlorine atom.

23. The method of claim 16, wherein preparing the doped silane comprises reacting a mixture comprising:

$$M*P(SiH_3)_2 \text{ and the } Si_nH_{m-y}X_y$$

to provide a heteroatom doped silane having a formula:

$$Si_nH_{m-y}(P(SiH_3)_2)_y$$

wherein M* is a metal atom containing moiety.

* * * * *

UNITED STATES PATENT AND TRADEMARK OFFICE
CERTIFICATE OF CORRECTION

| | |
|---|---|
| PATENT NO. | : 8,609,799 B2 |
| APPLICATION NO. | : 12/993239 |
| DATED | : December 17, 2013 |
| INVENTOR(S) | : Schulz et al. |

It is certified that error appears in the above-identified patent and that said Letters Patent is hereby corrected as shown below:

IN THE CLAIMS

Claim 14, Column 9, Line 42

"j" should be -- ; --.

Claim 16, Column 10, Line 9

"2n + 2" should be deleted.

Claim 17, Column 10, Line 17

"heteroatom" should be deleted.

Claim 17, Column 10, Line 19

"$Si_nH_{m-y}(PRSiH_4)_y$" should be replaced by -- $Si_nH_{m-y}(PRSiH_3)_y$ --.

Signed and Sealed this
Twenty-seventh Day of May, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,609,799 B2                                    Page 1 of 1
APPLICATION NO. : 12/993239
DATED            : December 17, 2013
INVENTOR(S)      : Schulz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 554 days.

Signed and Sealed this
Twenty-second Day of September, 2015

Michelle K. Lee
*Director of the United States Patent and Trademark Office*